United States Patent [19]

Urbahns et al.

[11] Patent Number: 5,719,181
[45] Date of Patent: Feb. 17, 1998

[54] USE OF ACYL-SUBSTITUTED AMINOPYRANS

[75] Inventors: Klaus Urbahns, Wuppertal; Hans-Georg Heine, Krefeld; Bodo Junge, Wuppertal; Frank Mauler, Seeheim; Reilinde Wittka, Köln; Jean-Marie-Viktor De Vry, Rösrath, all of Germany

[73] Assignee: Bayer Aktiengesellschaft, Leverkusen, Germany

[21] Appl. No.: 693,578

[22] Filed: Aug. 7, 1996

[30] Foreign Application Priority Data

Aug. 14, 1995 [DE] Germany ............ 195 29 859.4

[51] Int. Cl.⁶ .................... A61K 31/35; C07D 309/32
[52] U.S. Cl. .................. 514/459; 514/336; 546/282.1; 549/231
[58] Field of Search .................... 549/231, 424; 514/459, 336; 546/282.1

[56] References Cited

U.S. PATENT DOCUMENTS 3,897,462  7/1975  Meyer et al. ............ 260/345.8
3,966,767  6/1976  Meyer et al. ............ 260/332.2
3,974,290  8/1976  Meyer et al. ............ 424/283
4,622,332  11/1986  Wehinger et al. ............ 514/356

FOREIGN PATENT DOCUMENTS 0 088 276 A1  9/1983  European Pat. Off. .
1 402 793  8/1975  United Kingdom .
WO 96/06091  2/1996  WIPO .

OTHER PUBLICATIONS

N. Ibrahim, Heterocycles, vol. 24, No. 4, pp. 935–938 (1996).

P.W.L. Tas, et al., Neuroscience Letters, vol. 94, pp. 279–284 (1988).

*Primary Examiner*—Joseph McKane
*Attorney, Agent, or Firm*—Sprung Kramer Schaefer & Briscoe

[57] ABSTRACT

The invention relates to the use of acyl-substituted aminopyrans for the production of medicaments, in particular of medicaments for the treatment of disorders of the central nervous system.

7 Claims, No Drawings

USE OF ACYL-SUBSTITUTED AMINOPYRANS

The present invention relates to the use of acyl-substituted aminopyrans as medicaments, to novel active compounds and to a process for their preparation, in particular to their use as cerebrally active agents.

Some 2-aminopyrans are known as synthesis components from the publication Heterocycles (1986), 24 (4), 935–8. 2-Amino-4H-pyrans having an antihypertensive action are additionally described in DE 22 35 406.

It has now been found that the acyl-substituted aminopyrans of the general formula (I)

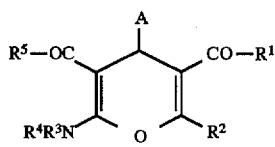

in which

A represents aryl having 6 to 10 carbon atoms or pyridyl, each of which is optionally substituted up to 3 times by identical or different nitro, cyano, phenyl, halogen or trifluoromethyl or by straight-chain or branched alkylthio or alkoxy each having up to 6 carbon atoms, $R^1$ represents straight-chain or branched alkyl having up to 8 carbon atoms, $R^2$ represents straight-chain or branched alkyl having up to 6 carbon atoms, $R^3$ and $R^4$ are identical or different and represent hydrogen or straight-chain or branched alkyl or acyl each having up to 6 carbon atoms, $R^5$ represents straight-chain or branched alkyl or alkoxy each having up to 8 carbon atoms, and their salts surprisingly have a modulating action on potassium channels and are thus suitable for use in the treatment of disorders of the central nervous system.

In the context of the invention, physiologically acceptable salts are preferred. Physiologically acceptable salts are in general salts of the compounds according to the invention with inorganic or organic acids. Preferred salts are those with inorganic acids, for example hydrochloric acid, hydrobromic acid, phosphoric acid or sulphuric acid, or salts with organic carboxylic or sulphonic acids, for example acetic acid, maleic acid, fumaric acid, malic acid, citric acid, tartaric acid, lactic acid, benzoic acid, or methanesulphonic acid, ethanesulphonic acid, phenylsulphonic acid, toluenesulphonic acid or naphthalenedisulphonic acid.

The compounds according to the invention can exist in stereoisomeric forms which either behave as image and mirror image (enantiomers) or which do not behave as image and mirror image (diastereomers). The invention relates both to the antipodes and the racemic forms as well as the diastereomer mixtures. Like the diastereomers, the racemic forms can also be separated into the stereoisomerically uniform constituents in a known manner.

Preferred compounds are those of the general formula (I) in which

A represents phenyl, naphthyl or pyridyl, each of which is optionally substituted up to 3 times by identical or different nitro, cyano, fluorine, chlorine, bromine, iodine, phenyl or trifluoromethyl or by straight-chain or branched alkylthio or alkoxy each having up to 4 carbon atoms, $R^1$ represents straight-chain or branched alkyl having up to 6 carbon atoms, $R^2$ represents straight-chain or branched alkyl having up to 4 carbon atoms, $R^3$ and $R^4$ are identical or different and represent hydrogen or straight-chain or branched alkyl or acyl each having up to 4 carbon atoms, $R^5$ represents straight-chain or branched alkyl or alkoxy each having up to 6 carbon atoms, and their salts, in the treatment of disorders of the central nervous system.

Particularly preferred compounds are those of the general formula (I) in which

A represents phenyl which is optionally substituted up to 3 times by identical or different nitro, cyano, fluorine, chlorine, bromine, iodine, trifluoromethyl or methoxy, $R^1$ is methyl or ethyl, $R^2$ is methyl or ethyl, $R^3$ and $R^4$ are identical or different and represent hydrogen or straight-chain or branched alkyl or acyl each having up to 3 carbon atoms, $R^5$ represents straight-chain or branched alkyl or alkoxy each having up to 4 carbon atoms, and their salts, in the treatment of disorders of the central nervous system.

They are modulators having selectivity for calcium-dependent and charybdotoxin-sensitive potassium channels, in particular of the central nervous system.

On account of their pharmacological properties, they can be employed for the production of medicaments for the treatment of central degenerative disorders, such as in the occurrence of dementias, multiinfarct dementia (MID), primary degenerative dementia (PDD), presenile and senile dementia in Alzheimer's disease, HIV dementia and other forms of dementia. They are further suitable for the treatment of Parkinson's disease or amyotrophic lateral sclerosis and multiple sclerosis.

The active compounds are furthermore suitable for the treatment of brain disorders in old age, organic brain syndrome (OBS) and of age-related memory disorders (age-associated memory impairment, AAMI).

They are suitable for the prophylaxis, treatment and control of the sequelae of cerebral circulatory disorders such as cerebral ischaemias, strokes, craniocerebral traumata and of subarachnoid haemorrhages.

They are useful for the treatment of depressions and psychoses, e.g. schizophrenia. They are additionally suitable for the treatment of disorders of neuroendocrine secretion and of neurotransmitter secretion and health disorders associated therewith, such as mania, alcoholism, drug abuse, dependence or abnormal eating behaviour. Further areas of application are the treatment of migraine, sleep disorders and of neuropathies. They are moreover suitable as analgesics.

The active compounds are further suitable for the treatment of disorders of the immune system, in particular T-lymphocyte proliferation and for affecting the smooth musculature, in particular of the uterus, urinary bladder and bronchial tract and for the treatment of diseases associated therewith, e.g. asthma and urinary incontinence, and for the treatment of high blood pressure, arrhythmia, angina, diabetes, sickle-cell anaemia, cancer, restenosis, chronic obstructive pulmonary disease and edema.

The invention additionally relates to new compounds of the formula (Ia)

and their salts, having the substituent meanings given in the following table:

| A | R¹ | R² | R³ | R⁴ | R⁵ |
|---|----|----|----|----|----|
| 2,3-diCl-phenyl | CH₃ | CH₃ | H | CO—CH₃ | OCH₃ |
| 2,3-diCl-phenyl | CH₃ | CH₃ | H | H | OCH₃ |
| 3,4-diCl-phenyl | CH₃ | CH₃ | H | H | OCH₃ |
| 3-NO₂-phenyl | CH₃ | CH₃ | H | H | OCH₃ |

Processes for the preparation of the compounds of the general formula (I) according to the invention have additionally been found, characterized in that

[A] ylidene compounds of the general formula (II)

in which

A, R¹ and R² have the meanings indicated above, are reacted, if R⁵=alkoxy (R⁵'), with compounds of the general formula (III) and, if R⁵=alkyl (R⁵''), with compounds of the general formula (IIIa)

in which

R⁵' and R⁵'' have the meanings indicated above, in inert solvents, if appropriate in the presence of bases, or

[B] ylidene compounds of the general formula (IV)

in which

A and R⁵ have the meanings indicated above, are reacted with compounds of the general formula (V)

in which

R¹ and R² have the meaning indicated above, in inert solvents and if appropriate in the presence of a base, and if R³ and/or R⁴≠H an alkylation or acylation according to customary methods follows.

The process according to the invention can be illustrated by way of example by the following reaction scheme:

Suitable solvents are all inert organic solvents which do not change under the reaction conditions. These preferably include alcohols such as methanol, ethanol, propanol or isopropanol, or ethers such as diethyl ether, dioxane, tetrahydrofuran, glycol dimethyl ether, or diethylene glycol dimethyl ether, acetonitrile, or amides such as hexamethylphosphoramide or dimethylformamide, or acetic acid or halogenated hydrocarbons such as methylene chloride, carbon tetrachloride or hydrocarbons such as benzene or toluene, or pyridine. It is also possible to use mixtures of the solvents mentioned. Methanol is particularly preferred.

Suitable bases are in general alkali metal hydrides or alkoxides, for example sodium hydride, sodium ethoxide or potassium tert-butoxide, or cyclic amines, for example piperidine, dimethylaminopyridine or $C_1$-$C_4$-alkylamines, for example triethylamine. Triethylamine or sodium ethoxide is preferred.

The base is in general employed in an amount from 1 mol to 5 mol, preferably from 1 mol to 2 mol, relative to 1 mol of the compounds of the general formula (II).

The reactions with compounds of the general formulae (III) and (IIIa) are in general carried out in a temperature range from 0° C. to 150° C., preferably from 40° C. to 80° C.

The reactions can be carried out at normal pressure, but also at elevated or reduced pressure (e.g. 0.5 to 3 bar). In general, the reactions are carried out at normal pressure.

Enantiomerically pure forms are obtained, for example, by separating diastereomer mixtures of the compounds of the general formula (I) in which $R^1$ represents an optically active ester radical according to a customary method, then either directly transesterifying or first preparing the chiral carboxylic acids and then preparing the enantiomerically pure compounds by esterification.

The diastereomers are in general separated either by fractional crystallization, by column chromatography or by countercurrent distribution. Which is the optimum process must be decided from case to case, sometimes it is also expedient to use combinations of the individual processes. Separation by crystallization or countercurrent distribution or a combination of both processes is particularly suitable.

The enantiomerically pure compounds are also accessible by chromatography of the racemic esters on chiral phases.

The compounds of the general formulae (II), (III), (IIIa), (IV) and (V) are known per se or can be prepared by customary methods.

Rubidium Efflux From C6-BU1 Glioma Cells

The experiments were carried out with slight modifications according to the method described by Tas et al. (Neurosci. Lett. 94, 279–284, (1988)). For this purpose, rat C6-BU1 glioma cells were used. From the data obtained by atomic absorption spectroscopy, the increase in efflux above the basal efflux caused by ionomycin is calculated and set as 100%. Stimulations in the presence of test substances are then related to this value.

The present invention also includes pharmaceutical preparations which, in addition to inert, non-toxic, pharmaceutically suitable auxiliaries and excipients, contain one or more compounds of the general formulae (I)/(Ia), or which consist of one or more active compounds of the formulae (I)/(Ia), and processes for the production of these preparations.

The active compounds of the formulae (I)/(Ia) should be present in these preparations in a concentration of 0.1 to 99.5% by weight, preferably of 0.5 to 95% by weight of the total mixture.

In addition to the active compounds of the formulae (I)/(Ia), the pharmaceutical preparations can also contain other pharmaceutical active compounds.

The abovementioned pharmaceutical preparations can be prepared in a customary manner by known methods, for example using the auxiliary(ies) or excipient(s).

In general, it has proved advantageous to administer the active compound(s) of the formulae (I)/(Ia) in total amounts of approximately 0.01 to approximately 100 mg/kg, preferably in total amounts of approximately 1 mg/kg to 50 mg/kg of body weight every 24 hours, if appropriate in the form of several individual doses, to achieve the desired result.

However, it may, if appropriate, be advantageous to depart from the amounts mentioned, namely depending on the type and on the body weight of the subject treated, on individual behaviour towards the medicament, the nature and severity of the disorder, the type of preparation and administration, and the time or interval at which administration takes place.

EXAMPLE 1

Methyl 5-acetyl-2-amino-6-methyl-4-(2,3-dichlorophenyl)-4H-pyran-3carboxylate

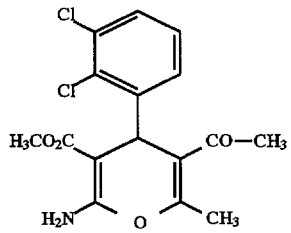

a) The mixture formed from 6.0 g(0.034 mol) of 2,3-dichlorobenzaldehyde, 3.4 g (0.034 mol) of pentane-2,4-dione and 3.9 g (0.034 mol) of methyl cyanoacetate in 75 ml of methanol is heated to reflux for 3 h and 40 min after addition of 0.5 ml of glacial acetic acid and 0.3 ml of triethylamine. After cooling, the methyl 2-cyano-3-(2,3-dichlorophenyl)acrylate which is precipitated is filtered off, the filtrate is evaporated in vacuo and the residue (10.5 g) is chromatographed on 300 g of silica gel using toluene/ethyl acetate ( 10: 1).

5.0 g of product are obtained.

M.p.: 142°–145° C. (capillary) (from dichloromethane/petroleum ether).

$R_f$: 0.26 (toluene/ethyl acetate=3:1)

$C_{16}H_{15}Cl_2NO_4$ Calc.: C 53.9% H 4.24% N 3.93% Found: 54.00% H 4.18% N 4.07% b) Methyl 5-acetyl-2-amino-6-methyl-4-(2,3-dichlorophenyl)-4H-pyran-3-carboxylate is also obtained from the reactions of 3-acetyl-4-(2,3-dichlorophenyl)-butene-2-one with methyl cyanoacetate and methyl 2-cyano-3-(2, 3-dichlorophenyl)acrylate with pentane-2,4-dione under the reaction conditions indicated above.

EXAMPLE 2

Methyl 5-acetyl-2-amino-6-methyl-4-(4,3-dichlorophenyl)-4H-pyran-3-carboxylate

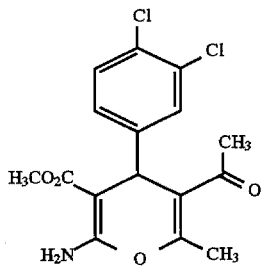

The title compound is prepared in analogy to the directions of Example 1.

Melting point: 181° to 185° C. (CH$_2$CH$_2$/PE)

EXAMPLE 3

Methyl 5-acetyl-2-acetylamino-6-methyl-4-(2,3-dichlorophenyl)-4H-pyran-3-carboxylate

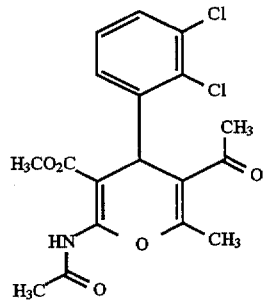

9.2 g (0.026 mmol) of methyl 5-acetyl-2-amino-6-methyl-4-(2,3-dichlorophenyl)o4H-pyran-3-carboxylate are heated at reflux for 30 min in 30 ml of acetic anhydride. After addition of 30 ml of methanol, the mixture is evaporated in vacuo, and the residue is stripped off twice in vacuo using 30 ml of toluene each time. Chromatography of the oily residue (9.1 g) on silica gel using toluene/ethyl acetate (3:1), the structure of which is verified by the H-NMR spectrum.

EXAMPLE 4

Methyl 5-acetyl-2-amino-6-methyl-4-(3-nitrophenyl)-4H-pyran-3-carboxylate

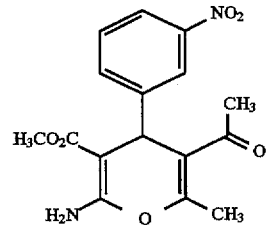

The title compound was prepared in analogy to the procedure of Example 1.

M.p.: 160°–163° C. (CH$_2$CL$_2$/PE)

We claim:

1. A method of treating a patient afflicted with a disorder of the central nervous system which comprises administering to such patient an amount effective therefor of an acyl-substituted aminopyran of the general formula (I)

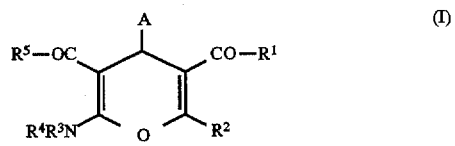

in which

A represents aryl having 6 to 10 carbon atoms or pyridyl, each of which is optionally substituted up to 3 times by identical or different nitro, cyano, phenyl, halogen or trifluoromethyl or by straight-chain or branched alkylthio or alkoxy each having up to 6 carbon atoms, $R^1$ represents straight-chain or branched alkyl having up to 8 carbon atoms, $R^2$ represents straight-chain or branched alkyl having up to 6 carbon atoms, $R^3$ and $R^4$ are identical or different and represent hydrogen or straight-chain or branched alkyl or acyl each having up to 6 carbon atoms, $R^5$ represents straight-chain or branched alkyl or alkoxy each having up to 8 carbon atoms, or a salt thereof.

2. The method according to claim 1, in which

A represents phenyl, naphthyl or pyridyl, each of which is optionally substituted up to 3 times by identical or different nitro, cyano, fluorine, chlorine, bromine, iodine, phenyl or trifluoromethyl or by straight-chain or branched alkylthio or alkoxy each having up to 4 carbon atoms, $R^1$ represents straight-chain or branched alkyl having up to 6 carbon atoms, $R^2$ represents straight-chain or branched alkyl having up to 4 carbon atoms, $R^3$ and $R^4$ are identical or different and represent hydrogen or straight-chain or branched alkyl or acyl each having up to 4 carbon atoms, $R^5$ represents straight-chain or branched alkyl or alkoxy each having up to 6 carbon atoms, and their salts, in the treatment of disorders of the central nervous system.

3. The method according to claim 1, in which

A represents phenyl which is optionally substituted up to 3 times by identical or different nitro, cyano, fluorine, chlorine, bromine, iodine, trifluoromethyl or methoxy, $R^1$ is methyl or ethyl, $R^2$ is methyl or ethyl, $R^3$ and $R^4$ are identical or different and represent hydrogen or straight-chain or branched alkyl or acyl each having up to 3 carbon atoms, $R^5$ represents straight-chain or branched alkyl or alkoxy each having up to 4 carbon atoms, and their salts, in the treatment of disorders of the central nervous system.

4. Acyl-substituted aminopyrans selected from the group consisting of methyl 5-acetyl-2-amino-6-methyl-4-(2,3-dichlorophenyl)-4H-pyran-3-carboxylate of the formula

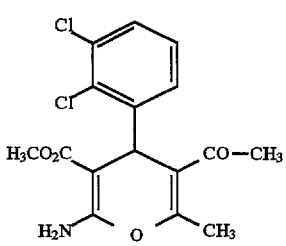

methyl 5-acetyl-2-amino-6-methyl-4-(4,3-dichlorophenyl)-4H-pyran-3-carboxylate of the formula

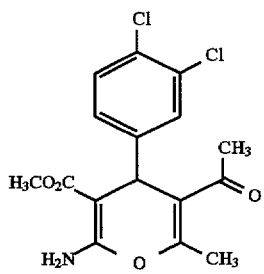

methyl 5-acetyl-2-acetylamino-6-methyl-4-(2,3-dichlorophenyl)-4H-pyran-3-carboxylate of the formula

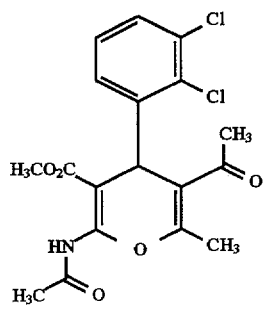

and methyl 5-acetyl-2-amino-6-methyl-4-(3-nitrophenyl)-4H-pyran-3-carboxylate of the formula

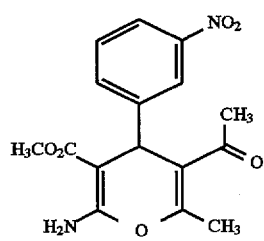

or a salt thereof.

5. Process for the preparation of the compounds according to claim 4, wherein

[A]ylidene compounds of the general formula (II)

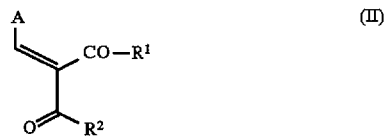

in which

A represents aryl having 6 to 10 carbon atoms or pyridyl, each of which is optionally substituted up to 3 times by identical or different nitro, cyano, phenyl, halogen or trifluoromethyl or by straight-chain or branched alkylthio or alkoxy each having up to 6 carbon atoms, $R^1$ represents straight-chain or branched alkyl having up to 8 carbon atoms, $R^2$ represents straight-chain or branched alkyl having up to 6 carbon atoms, are reacted, if $R^5$=alkoxy ($R^{5'}$), with compounds of the general formula (III) and, if $R^5$=alkyl ($R^{5"}$), with compounds of the general formula (IIIa)

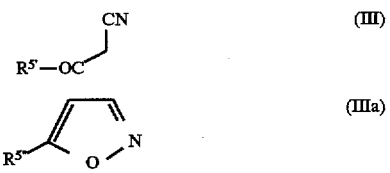

in which $R^{5'}$ and $R^{5"}$ have the meanings indicated above, in inert solvents, if appropriate in the presence of bases, or

[B]ylidene compounds of the general formula (IV)

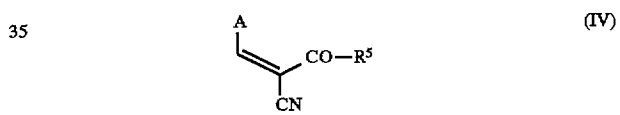

in which $R^5$ represents straight-chain or branched alkyl or alkoxy each having up to 8 carbon atoms, are reacted with compounds of the general formula (V)

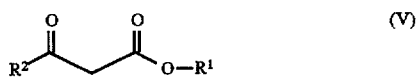

in inert solvents and if appropriate in the presence of a base.

6. A method of treating a patient afflicted with a disorder of the central nervous system which comprises administering to such patient an amount effective therefor of an acyl-substituted aminopyran or salt thereof according to claim 4.

7. A pharmaceutical composition for treating a patient afflicted with a disorder of the central nervous system comprising an amount effective therefor of an aminopyran or salt thereof according to claim 4 and a diluent.

* * * * *